United States Patent [19]

Clayton

[11] 4,403,982
[45] Sep. 13, 1983

[54] COLON CLEANSING SYSTEM AND TECHNIQUE

[76] Inventor: Ralph S. Clayton, 1309 Canterbury Dr., Abilene, Tex. 79602

[21] Appl. No.: 185,037

[22] Filed: Sep. 8, 1980

Related U.S. Application Data

[63] Continuation of Ser. No. 937,591, Aug. 28, 1978, abandoned.

[51] Int. Cl.³ .............................................. A61M 3/00
[52] U.S. Cl. .................................................... 604/28
[58] Field of Search ........... 128/227, 245, 246, 349 B, 128/349 BV

[56] References Cited

U.S. PATENT DOCUMENTS 3,075,526 1/1963 Morris .................................. 128/227
3,399,677 9/1968 Gould et al. ................... 128/349 BV
3,459,175 8/1969 Miller ............................. 128/246 X
3,765,413 10/1973 Lepar .................................... 128/245

OTHER PUBLICATIONS

Physicians' Desk Reference, Fleet ® Brand Bisacodyl Enema, p. 820, Feb. 1977.

Primary Examiner—John D. Yasko
Attorney, Agent, or Firm—Larson & Taylor

[57] ABSTRACT

According to the present system and technique, with the patient lying on his right side, a soap containing enema solution, preferably with a laxative therein, is introduced into the colon through the anal opening via a suitable tube held in the rectum by an inflated balloon (18), preferably from a bag (11) held above the patient, in a volume, usually sufficient to completely fill the colon all the way to the cecum, usually 1500 cc to 3000 cc in a normal adult. Inflation of the balloon can be accurately controlled by using a calibrated syringe (40), acting through a suitable valve containing conduit (21). The balloon and tube can be further secured in place with a limiting means (19) on the tube outside of the patient's anal opening and/or with specially made device (60) designed to squeeze the patient's buttocks together.

62 Claims, 15 Drawing Figures

LEGEND FOR FIGS. 9A-9E

UNLOOSENED FECAL MATTER

GAS

LOOSENED FECAL MATTER

LIQUID SOLUTION

SHOWS WALL PORTION WASHED BY LIQUID SOLUTION PRIOR TO PATIENT MOVEMENT (FIG. 9B, 9C, 9D)

SHOWS WALL PORTION WASHED BY LIQUID SOLUTION BY RIGHT SIDE DOWN TECHNIQUE AFTER ROLLED TO LEFT SIDE (FIG. 9D)

BEFORE STARTING

COLON CLEANSING SYSTEM AND TECHNIQUE

This is a continuation, of application Ser. No. 937,591 filed Aug. 28, 1978 now abandoned.

DESCRIPTION

1. Technical Field

This invention relates to an improved method and technique for cleansing the colon.

2. Background of the Invention

There are of course numerous situations which require emptying the colon of solid fecal material, liquid or gas. Healthy persons could need such a cleansing for any one of a number of reasons including constipation. In addition it would be required in a number of medical situations including preparation for conducting tests, preparation for surgery and routine emptying of the colon for patients such as paralyzed persons or any person who cannot perform this function naturally. Preparation for testing would include essentially emptying of the colon of solids, liquid or gas prior to injecting therein a barium enema for visual observation under an x-ray machine. It is preferable to empty the colon for virtually any type of surgery in which an anesthetic is used, even if the surgery does not involve opening up the thoracic cavity or the abdomen since fecal material or gas in the colon exerts a pressure on the diaphragm, hence imposing limitations on the ability of the patient to breath, and this in turn can lead to collapse of the lungs, pneumonia, vomiting and other problems. Disabled persons such as fecally incontinent persons would include those disabled by age as well as those paralyzed below the waist, or disabled for any reason.

Present systems for attempting to cleanse the colon include two basic procedures; first the use of enemas for the lower colon (from the splenic flexure to the anal opening) and second, the use of oral laxatives for clearing out the upper colon (from the splenic flexure to the cecum). The giving of enemas normally includes multiple enemas of less than 1000 cc, normally approximately 500 cc each, which, incidentally, are often inadequate, while having the patient lay on his or her (referred to generically hereinafter as "his") left side. In practice the limit may be approximately 500 cc since above this level the enema solution will tend to leak out of the anal opening around the tube and onto the bed. A single enema of this type is almost never sufficient to cleanse out the entire lower colon so that the nurse or aide is normally given directions to continue giving additional enemas using the same volume of liquid, i.e. about 500 cc, usually until the expelled liquid is "clear". At this time the usefulness of the enema procedure is considered terminated and as noted above any additional waste material within the patient's upper colon is removed by having the patient take laxatives orally and waiting the necessary time until such orally taken laxatives pass completely through the patient's stomach and small intestine, supposedly or with the purpose of cleansing the upper colon including the cecum, the ascending colon, the hepatic flexure, and the transverse colon, urging the solid waste material into and hopefully out of the already cleansed lower colon. Or the enemas may be given after the laxatives.

Although the above described use of the enema concept, i.e. essentially for cleaning only the patient's lower colon, has been used since the immemorial, such procedure has certain significant disadvantages. Multiple enemas are physically exhausting to the patient. Moreover, they can cause dehydration of the patient's body with the attendant loss of water and electrolytes, thereby upsetting both the moisture and electrical balance of the patient's body. This of course can have severe repercussions on the operation of vital organs including the heart. Further multiple enemas irritate the anus and internal lining of the colon and this can be very dangerous, especially in the case of aged patients or those with a diseased colon. In addition to the physical disadvantages, because of the odors and mess of enemas there are the psychological disadvantages of humiliation and embarrassment. In addition to the physical and psychological effects on the patient, there are the very considerable monetary disadvantages in this age of sky-rocketing hospital costs. The procesure of giving multiple enemas followed or preceded by the giving of oral laxatives to complete cleansing of the colon will require in virtually all cases at least one additional day in the hospital, with its attendant costs.

Hence, there exists a need for a new and improved system and technique for more effectively cleansing the colon.

SUMMARY OF INVENTION

It is a purpose of the present invention to provide a new system and technique for cleansing the colon. More particularly, its purpose is to provide new system and technique so significantly advanced relative to previously known procedures that it will permit cleansing of the entire colon from the cecum, including the ascending, transverse and descending colons, to the anal opening, in a single injection of a cleansing solution.

The present invention is based initially on an analysis of the conventional procedure for giving enemas, with and without oral laxatives, the shortcomings and defects of these procedures, and the reasons for such shortcomings and defects. In accordance with the conventional enema procedure, the patient is placed on his left side so that the enema solution can flow "downhill" from the anal opening toward the descending colon located on the left side. This is entirely consistent with the purpose of a conventional enema procedure, which apparently is to cleanse only up to and through the descending colon to the splenic flexure. This well recognized limitation of the conventional enema procedure probably resulted because, inter alia, once a sufficient volume of enema solution was introduced to fill the colon up to the splenic flexure, i.e. including the rectum, the sigmoid and the descending colon, the patient could hold no more liquid, and any additional liquid would simply leak out between the walls of the anal opening and the outer surface of the enema tube. In any event, as discussed above, the remaining portions of the colon, the ascending and transverse colon are not cleansed by the conventional enema but are cleaned by the use of laxatives and the like.

Upon analyzing the conventional enema procedure, with and without the use of orally taken laxatives, and upon noting the well recognized limitations thereof, I made several discoveries. First, I ascertained the reasons for the well accepted limitations on the conventional enema procedures and I recognized that whatever reasons historically supported these limitation, they were not valid. For reasons set forth above, the patient is placed with his left side down. I recognized that liquid then entering the rectum, sigmoid and descending colon would then reach a barrier at the splenic flexure which could not be crossed. Beyond the splenic flexure, the liquid would be travelling uphill. But located in the colon beyond the splenic flexure is a body of fecal matter and gas which together form a gas lock opposing the flow of cleansing fluid upwardly into and through the transverse colon. That is, the solid fecal matter and the gas are relatively fixed in place, not easily moved, such that further movement of the enema solution would oppose gravity in two ways, the upward movement of the liquid and the downward movement of the gas. This problem is aggravated by the fact that the liquid entering the descending colon would flow under any gas located therein, forcing that gas upward into the transverse colon, thus enlarging the body of gas which the liquid would have to cross, opposing gravity, to enter the transverse colon. Some have suggested altering the conventional enema procedure slightly by placing the patient on the right side rather than the left side. This did allow some of the enema liquid reaching the splenic flexure to run down the transverse colon, possibly entering the ascending colon. However, considering the small volume of liquid used in the conventional enema procedures, and absent recognition of my subsequent discoveries to be discussed below, this alternative did not come close to cleansing the entire colon.

A further discovery involved an analysis of the actual mechanics of the interaction between the solid fecal matter or "stool" and the anatomy of the colon. A significant problem in cleansing the colon is that the stool and the sticky mucus material within the colon become attached to the lining of the colon and must be detached. Recognizing that the colon stretches, whereas the stool and mucus material do not stretch, I recognized that such detachment could be brought about by causing distension of the colon throughout its entire length. I accomplished this distension by introducing into the patient not the conventional volumes of liquid solution but a much greater volume, namely whatever volume is necessary to completely distend the colon and fill all inteerstices between the stool material and the colon lining, except of course for the volume thereof occupied by gas, all the way from the anal opening to the cecum. I accomplished this by placing the patient on his right side and introducing the necessary quantity of liquid solution into the patient while sealing the anal opening by a balloon device to prevent any portion of this larger quantity of liquid from leaking out of the anal opening around the exterior of the liquid tube. I found that introducing liquid in this manner worked quite differently from a conventional left side down enema procedure in many respects. Firstly, initially liquid does not cleanse the descending colon as well as the left side down procedure since gases will now have risen to and collected at the "top" of the descending colon ("top" meaning the uppermost part when the patient is on his right side) and the liquid solution entering the colon will pass beneath these gases. But when the liquid then reaches the splenic flexure it easily runs down the transverse colon, easily displacing gases therein which further collect in the descending colon. Soon the liquid fills the ascending colon. This, to my knowledge, was the first time that anyone had utilized an enema solution in such a manner as to completely fill the ascending colon. A point is soon reached when the colon is essentially completely full of fecal matter, gases and liquid throughout its entire length, whereupon it begins to enlarge or "distend", i.e. stretch, and since it is full throughout its length, this stretching will take place completely from one end to the other end, i.e. from the anal opening to the cecum. Such stretching will cause the walls of the colon to detach from the stool and mucus attached thereto which of course do not stretch along with the colon walls.

I have further found that best results are achieved by combining this distention with an agitating washing action, preferably employing mechanical agitation. This is preferably accomplished by rolling the patient to the left side down position and possibly back to the right side down position, and possibly repeating this procedure several times. This causes the liquid in the ascending and transverse colons partially to flow back through the transverse colon, displacing the gas in the descending colon which now moves back up the transverse colon, the effect of this being to permit the liquid to contact the entire inner lining of the colon, while agitating same, along the entire inner surface of the colon. Summarizing, the colon is distended to some extent, causing an initial separation of the colon from the attached mucus and stool material, and in this state the entire inner lining of the colon may be washed and concurrently mechanically agitated. The stool and mucus, thus separated, are more readily capable of being expelled.

In carrying out the present invention, I would preferably use a liquid solution containing a lubricant, preferably castile soap. As is shown, castile soap assists in softening and fragmenting the stool. The soap also lubricates the fecal matter and the lining, thus facilitating expulsion of the fecal matter. What is new, however, is that prior to the present invention, the advantages of such a lubricant were realized only with respect to the descending colon, whereas utilizing the present invention, these advantages are experienced throughout the entire length of the colon. Additionally, the ability of this lubricant to stimulate contractions of the colon can now be experienced throughout the entire length of the colon, in cooperation with the above described distention of the entire colon, thus for the first time providing means for cooperatively distending and contracting the entire colon, throughout its length, with its attendant increased ability to expel all solid and gaseous material throughout the entire length of the colon.

I have further discovered that my new technique is enhanced by including a laxative in the liquid solution, and as a result thereof I have discovered a new way to administer a laxative. Heretofore, either laxatives and/or adequate volumes of water have been taken orally. The delay in gastric emptying and the variable small intestinal transit time and absorption make the results unpredictable and uncontrollable. A laxative can have no effect or can cause violent purging, resulting in severe proctitis, and exacerbation of hermorrhoids occurs, and there is a risk of perforating a diseased colon. Moreover, what does arrive at the colon arrives only at the cecum. If the patient has hard, impacted fecal material in his transverse colon and/or descending colon, the laxative action in the ascending colon can be disadvantageous and indeed extremely dangerous since it can perform its function at that location but be insufficient to break the impaction in the downstream areas, resulting only in painful cramping, exhaustion and dehydration of the patient, not to mention the imbalancing of the patient's electrolytes. Another recently developed technique has been to place a laxative in a container having 37 cc of an aqueous enema solution and to introduce such solution into only the lowest 10 cm or so of the colon including essentially the anal canal and the rectum.

A discovery of the present invention is that my technique of completely filling and distending the colon with enema solution can further encompass the inclusion therein of a laxative material, whereby for the first time such laxative material can be uniformly and reliably carried directly to the entire mucosa of the colon from the anal opening to the cecum, uniformly contacting the mucosa over its entire length as the mucosa distends and separates from the fecal material located therein under the force of the liquid completely filling the colon, thereby avoiding the delays and other disadvantages of orally taken laxatives. Never prior to this invention, to my knowledge, has there been any method or procedure for carrying a laxative ingredient directly and uniformly to the entire length of the colon as is accomplished in the manner expressed above. An additional advantage of applying a laxative to the entire colon in this manner is that if a pool of fluid remains in any segment of the colon, after the first defecation session, the correct concentration of laxative is present in the fluid and provides a continuous stimulation to that segment of the colon, resulting in complete expulsion of the contents of the colon. Contrasting this with the use of a non-laxative liquid solution, if a pool then remains at any location in the colon, since it does not contain laxative to stimulate expulsion, there is thus incomplete expulsion of the contents of the colon.

Another feature of the present invention is the provision of an enema solution containing both a soap for providing lubricating properties and a laxative ingredient. One laxative ingredient which I have found to be advantageous for this purpose is non-soluble Bisacodyl carried in an aqueous suspension.

The use of soap and Bisacodyl solution is safer than water enemas since it is more nearly isotonic (the same osmotic pressure as the tissues and hence will not be absorbed) thereby avoiding fluid and electrolyte imbalance risks which occur with respect to water enemas. The soap and Bisacodyl are much safer than oral laxatives and oral purgatives.

As described above, the present system and technique employs an inflatable balloon at the end of the enema solution tube to hold in the necessary volume of liquid solution. Such a balloon has the additional advantage in the present invention of permitting the patient to relax, thereby relaxing the abdominal wall muscles and allowing greater and more comfortable distention of the colon throughout its length and hence stimulating better contractions. However, such balloons do present certain problems, solutions to which form a part of the present invention. When inflating the balloon there is no way to visually observe the size of the balloon within the patient. It has been known and documented that in numerous cases a balloon has become overinflated and, especially in the case of a diseased colon, has ruptured the colon, resulting ultimately in the death of the patient. Attempts to limit the amount of air inflated into such a balloon have included a small puffer of a known size and capable of a single puff. However, such devices are unreliable since they do not take into account the residual air present in a balloon prior to inflation and they do not measure exactly the volume of air injected. Moreover, at best such devices provide only an upper limit, i.e. they do not permit complete control over the volume of air in the balloon at all times.

In accordance with another feature of the present invention, I have provided a technique for absolutely controlling the volume of air within the balloon at all times. Such arrangement includes attaching the conduit which leads to the balloon to one end of a conventional syringe with calibrated markings thereon. The conduit should preferably include a spring loaded one-way valve normally closing this conduit but opened by the end of the calibrated syringe when it is attached to the conduit. If the balloon is of the type having residual air therein, then the syringe can be applied and the piston therein withdrawn to completely evacuate the balloon. This of course has the advantage of providing a minimal size of the balloon to facilitate insertion of the tube and balloon within the patient. The calibrated syringe would then be separated from the conduit (closing the valve) after which the piston therein would be reset back to its rearwardmost position, after which the calibrated syringe would be reconnected to the conduit, opening the valve, and the piston moved within the syringe by an amount positively known by observing the calibrated markings, whereby the operator could very closely control and visually observe the precise volume of air delivered to the balloon and therefore the size of the balloon. Indeed, as has not been possible heretofore, with this technique, the operator can increase or decrease the size of a balloon already in a patient by precisely determined amounts, to alleviate pain or otherwise meet changing conditions, all the time having complete knowledge of the volume of air in the balloon and therefore the size of the balloon.

Another characteristic of balloons as have been used heretofore for holding tubes within patients is that they are subjected to asymmetrical and significant forces tending to tilt the balloon and otherwise pull it up into the rectum whereby it will not perform its sealing function. In the past, balloons have been stabilized in place by pulling on the enema tube or by means of a bar, disc or the like located on the tube outside of the patient and exerting a force on the balloon holding it down into sealing contact with the rectum adjacent the anal canal. However, these bars, discs and the like have tended to be inadequate since they have not in all cases perfectly adapted to different size patients. Also, a bar or the like extending essentially fore and aft will not prevent tilting of the balloon about the fore and aft axis of the patient and hence will not completely stabilize the balloon in place. These disadvantages are overcome in accordance with the feature of the present invention whereby a hard or firm oval or circular disc is atttached to the tube at a location farther from the balloon then will be desirable for any given patient but arranged such that it can slide in only one direction, namely towards the balloon. In combination therewith, the tube can have indicia thereon marking positions for different size patients, i.e. one for a very thin patient, one for a normal patient and one for a heavy patient. Then, after the balloon has been inflated within the patient, and pulled down snugly over the lower opening of the rectum, the disc can be slid toward the balloon, stopping at the appropriate marker, whereat it will prevent the balloon from moving up away from the lower opening of the rectum.

As another feature of the invention, the disc can be connected with suitable straps, one in the rear and two in the front, each off center to pass to each side of the genitals, for connection to a waistband or the like on the patient, thereby preventing involuntary expulsion of the balloon and tube. The disc with the straps attached thereby stablizes the balloon against movement in either direction, i.e. in or out.

A system for carrying out the present method will further include a bag for holding the enema solution and a tube leading from the bag and to which the balloon would be attached for insertion into a patient. The bag should of course be of a large enough size to hold the desired quantity of enema solution which can desirably be as high as 3000 cc. Such bags have been used heretofore for barium enemas since barium fills the entire colon. However, bags intended for cleansing the colon have of course not been of this size. The tube leading from the bag to the patient must be of the smaller size conventionally used for enema solutions and not of the much larger type used heretofore for barium enemas. One reason for this is that the thicker barium tubes are required because of the heavy density of the barium material. However, enema solutions are essentially aqueous solutions which are much less dense than a barium enema. A smaller size tube is required to restrict the rate of liquid flow therethrough to an appropriate rate. It has been found for example that too rapid a flow of liquid into the colon will tend to distend the colon walls very rapidly, thus causing pain to the patient. It has been found that pain is sensed not by the extent of distention of the colon walls, since full distention will merely give a sensation of fullness, not pain, but rather, by the rate of distending, or stretching.

Another feature of my invention is to provide the liquid tube with a smooth rounded tip with small openings on the side. With such a tube, insertion is safer and more comfortable, avoiding injury to the anus or anterior wall of the rectum, or perforation of the rectum wall, as could more likely occur with a flat tip. Also it is less likely that the side holes would occlude with feces.

Another advantageous feature of the present invention is the limitation on the length of tube from the enema solution bag to the patient. Prior enema kits include a tube approximately 60 inches or 150 cm in length, which, if fully extended, subjects a patient's rectum to the considerable pressure of 150 cm of water, which is unnecessary in most cases and very dangerous in that it can cause rupture of a weak or diseased colon, and in fact has done so in some documented cases, resulting in the death of the patient. As a safety factor, therefore, I would limit the length of the tube to approximately 25-30 inches or 60-75 cm since this provides an adequate pressure head, without the attendant dangers of too great a head.

The balloon used in the present invention should preferably be of a type having a large dimension perpendicular to the wall of the tube as compared with its dimension parallel to the axis of the tube. Such a balloon, however, is necessarily of the type having a residual quantity of air in the balloon even in its most relaxed condition. In accordance with the present invention, such a more desirable balloon can be utilized, notwithstanding the residual air, by combining same with the above described calibrated syringe and valve arrangement since the latter can be used to completely evacuate even this residual air.

A patient will always have an urge to completely expel any device held within his anal opening, such as the tube and balloon. I have successfully prevented such expulsion by various means including straps attached to the disc as described above. As another advantageous feature of the present colon cleansing system and technique, I have provided a device which causes the patient's buttocks to be squeezed together along the mid-plane and against the perineum of the patient and held in that position while the balloon is in place in the patient. In accordance with the present invention, this device is so constructed that it can be applied to the patient after the liquid introduction tube and its balloon have been inserted into the patient and so as not to interfere therewith. In accordance with a preferred arrangement, this device comprises a band which wraps around the patient and which includes straps at its ends which can be sequentially connected, starting from the bottom and working upwardly.

The specific manner of applying the method of the present invention will vary for different situations and different patients. However, briefly summarizing the method of the present invention for a typical patient wherein it is required to cleanse the entire colon, but wherein the patient has no highly specific problem associated with the colon such as a diseased or weak colon or the like, such a general procedure would be as follows. The bag would first of all be filled with a suitable volume of liquid solution, for example approximately 2000 to 3000 cc of a castile soap aqueous solution having therein approximately 10 to 20 mg, or more, of Bisacodyl in aqueous suspension. This bag would also have associated with it a liquid tube leading therefrom with a suitable clamp thereon and at the end thereof a balloon adapted to be inflated at a later time within the patient and an oval disc adapted to be moved up against the patient. The patient would then be placed on his right side. A syringe would be connected to the conduit leading to the balloon to withdraw residual air, thereby completely collapsing the balloon. Standing in front of the patient, the nurse would then insert the end of the tube and the balloon into the patient's anal opening and the calibrated syringe would be moved a specific amount, as observed on the calibrated markings on the syringe to inflate the balloon to a precise predetermined size. The disc located on the tube is slid therealong to secure the tube and balloon in place in the patient. If the patient is of the type which might expel the balloon, straps or the device for squeezing the buttocks together and against the perineum can then be applied if desired, to keep the tube and balloon in place in the patient. The clamp is then opened, permitting the liquid solution to flow through the tube and into the patient. The liquid at this time has a sufficient head to flow "uphill" (with the patient on its right side) along the rectum and sigmoid and along the descending colon. The liquid then flows downwardly along the transverse colon, displacing upwardly to the descending colon any gases located therein. The liquid then continues its movement along the ascending colon to the cecum. After liquid has reached the cecum, thereby filling the colon (i.e. filling the interstices in the colon between the pieces of stool, and not taken up by gas in the colon), the next phase is entered, whereby this liquid tends to distend the lining of the colon which has the capability of stretching, said action thereby separating the lining from the fecal material located therein by shearing forces since the fecal material does not stretch. If the rate of flow of the liquid into and through the colon is kept at a relatively slow rate, the distention of the colon will not be too fast, and consequenty the patient will feel only a sensation of fullness, but not pain. This separation of the colon from the fecal material therein tends to expose the surface of the mucosa to the liquid which has been introduced.

Hence the laxative ingredient included therein can now reach the entire lining of the colon in a uniform manner not possible with any other procedure of which I am aware. The liquid is held in the patient for a short period of time. Although the emphasis of my method is "right side down" during insertion, during the holding period the patient will preferably be rolled several times to a left side down position to detach stool and mucus and to permit the liquid to move into those portions of the descending colon where gases may still be located to permit the liquid solution, including the laxative ingredient therein, to contact the mucosa in those portions. The patient is then taken to a suitable receptacle, the balloon is deflated, any straps or devices squeezing the buttocks together are released, the tube is removed and the patient at this time can expel the entire contents of the colon including all of the liquid and all of the solid material and gases therein.

As noted in the preceding paragraph I have found it advantageous for the nurse to stand in front of the patient as contrasted to the conventional technique of standing behind the patient. In front the nurse can observe the patient's reactions more accurately and communicate with the patient more effectively than if standing behind the patient. Also the nurse, standing in front, need not lose contact with the patient when assisting the patient off of the bed and to the potty chair or toilet. Otherwise, if standing behind the patient, the nurse would have to leave the patient's side and move around the foot of the bed to the other side to assist the patient. Finally it is much safer for the nurse to stand in front of the patient as it eliminates the possibility of the nurse being soiled by feces as could occur if the nurse were standing behind the patient and the patient involuntarily expelled the balloon.

Tests to date indicate that the single procedure is effective to remove more than 95% of the fecal material and gas in over 95% of the cases tested. If removal of more nearly 100% of the fecal material is desired for any reason, the entire procedure can be quickly and easily repeated as often as necessary. The present concept of cleansing the entire colon in a single procedure has the advantages, as compared to the conventional enema, of avoiding the risks, humiliation, embarrassment and the indignity of multiple enemas and the humiliation, embarrassment and indignity of the unpredictable results of laxatives given orally. Moreover, precisely because the entire colon is cleansed, leaving no feces in the ascending or transverse colons, fecal impaction is prevented, as are the dangers of repeated digital fragmentation of impacted feces, and its associated humiliation and embarassment. Also eliminated is the humiliation, embarrassment and indignity of accidental bed soiling (a) due to leakage of the enema liquid during the conventional enema procedure, this being prevented by the use of a balloon, and (b) due to subsequent involuntary expulsion of fecal matter, especially in the case of fecally incontinent patients, this being prevented by the fact that the entire colon was cleansed in the first place. Moreover, the risk of infection from soiling of the patient, the bed linen and the nurse with feces is minimized. Additionally there are the significant cost savings since a colon can be completely cleansed in a single hour rather than by an ~hour overnight program. Less personnel time and less equipment are required. The costs of changing and laundering soiled bed linen and bathing the patient are virtually eliminated.

Hence, it is an object of the present invention to provide a new and improved system and technique for cleansing the colon.

It is another object of the present invention to provide a new system and technique for cleansing the colon wherein the entire colon can be cleansed in a single operation.

It is another object of this invention to provide a new material as a vehicle and a new system for carrying a laxative ingredient uniformly to the entire lining of the colon.

It is another object of this invention to provide a new system and method for safely inflating a balloon adapted to hold a tube in the anal opening of a patient.

It is another object of the present invention to provide a new device for positively holding a tube and its inflatable balloon within a patient by moving the patient's buttocks together and against the patient's perineum.

It is still another object of this invention to provide a new and novel system for carrying out the above objects, which system is new, and which includes a number of separate integers which work with each other, many of which integers are themselves new.

These and other objects and advantages of the present invention will become apparent from the detailed description to follow.

BRIEF DESCRIPTION OF DRAWINGS

There follows a detailed description of preferred embodiments of the invention to be read together with the accompanying drawings wherein:

FIG. 9A illustrates the colon filled with solid waste material and gases prior to any cleansing.

FIG. 9B illustrates the functioning of a colon using a conventional enema procedure.

FIGS. 9C through 9E illustrate the functioning of a colon when cleansed in accordance with the present invention.

DETAILED DESCRIPTION

Figure 1:
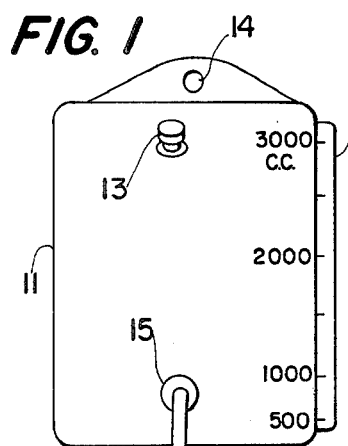
FIG. 1 is a schematic view showing certain elements arranged for use in accordance with the system and method of the present invention.

There follows a detailed description of the preferred method and system of the present invention. Whenever, in this discussion, reference is made to the drawings, like elements are represented by like numerals throughout the several views.

Referring now to FIGS. 1 through 5, there is shown and described those elements which comprise the system or apparatus for carrying out my new colon cleansing technique.

The system 10 would include a solution bag 11 for storage of cleansing solution. The bag would be of a conventional character and in fact can be of the type now sold by Bard, except that it would have a larger volume, for example a volume of over 2000 cc, and preferably 2500 or 3000 cc. Such a bag would be provided with graduations 12 and an opening 13 at the upper end, such as an unscrewable watertight cap for introducing liquid into the bag. A suitable aperture 14 may be provided at the very top for hanging the bag on a hook in use.

At its lower end, the bag 11 would include a connection 15 to a tube 16 for delivering the liquid solution to the patient. The tube would include a suitable clamp 25 thereon. It is important that the tube 16 be of a type and size appropriate for delivering an aqueous liquid solution to the patient, as contrasted with other types of tubes which are larger and stiffer for delivering thicker liquids such as barium enemas. One suitable tube for this purpose has an inside diameter of 3/16 of an inch and an outside diameter of ¼ inch, leaving a thickness of 1/16 of an inch. The thickness may preferably vary in the range between 1/32 of an inch and 1/16 of an inch. There are several reasons for preferring, if not requiring a tube of a suitable type. Firstly, if it is preferred to use a tube which extends more than a minimal distance beyond the balloon (such as balloon 18 to be described in greater detail below), then that end of the tube will engage the inside wall of the rectum as it is inserted therein, and unless it is soft enough and thin enough to bend up within the rectum, the tube may cause injury to the wall of the rectum and pain or injury to the prostate (in a male) or cervix (in a female) located immediately therebeyond. Secondly, a small inside diameter tube is required for the proper rate of liquid flow. Pain is caused in the patient not by the insertion of a large quantity of liquid (this will only provide a sensation of fullness) but by a rapid introduction of such liquid which results in excessively rapid distention and stretching of the lining and wall of the colon. This is especially important in cases where there is an obstruction or a diseased colon which might be friable and tear easily. A torn colon can result in infection and death.

Another advantageous characteristic of the tube 16 is its length which heretofore has been provided in most enema kits approximately 60 inches long, which length is unnecessary and dangerous in that it makes possible the placing of the bag a full 60 inches above the patient, thus providing a pressure or head equal to 60 inches of water felt by the patient. This is excessive, unnecessary, and can cause rupture of the colon, especially in the case of an aged or diseased colon. Hence, a feature of the present invention is that the tube 16 is limited to approximately 30 inches or 60-75 cm, thereby acting as a safety measure preventing the bag from being placed at too great a height above the patient.

Figure 2:
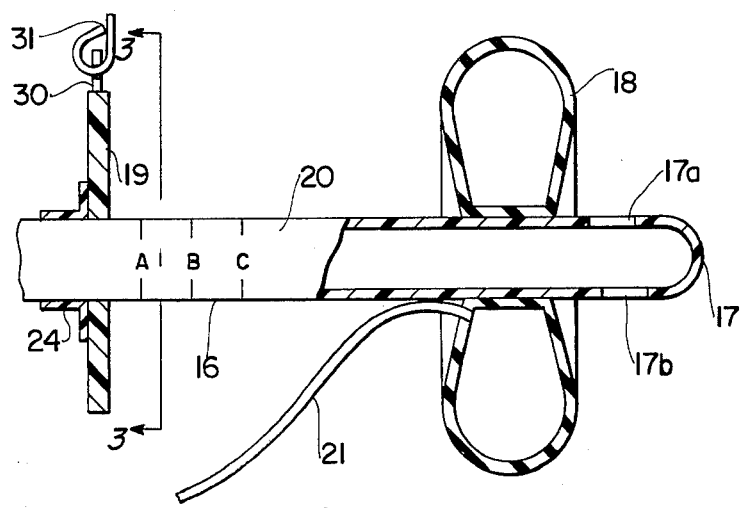
FIG. 2 is an enlarged view of a portion of FIG. 1, with certain elements shown in cross-section.
Figure 3:
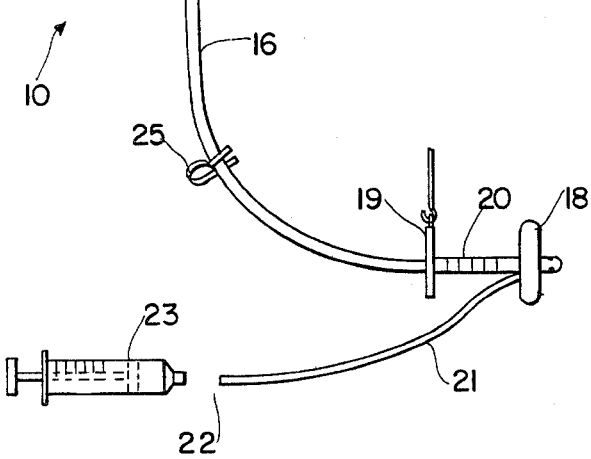
FIG. 3 is a sectional view taken along line 3—3 of FIG. 2.
Figure 3:
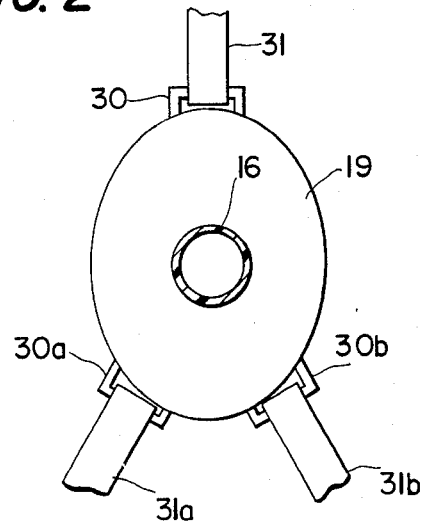

The end of the tube remote from the bag is shown in FIG. 1 and associated elements thereof are shown in greater detail in FIGS. 2 and 3. The remote end 17 is preferably a solid rounded end with a pair of openings 17a and 17b on the side thereof. The smooth rounded tip is safer to insert past the delicate anal tissues and is less likely to damage the anterior (front) wall of the rectum. Also, the side holes on the tip are less likely to occlude with fecal matter. Referring to these figures, near the remote end 17 of the tube 16, there is provided an inflatable balloon 18, which balloon is deflated completely during insertion, and then inflated after being inserted, said balloon located at the lower end of the rectum, thereby holding the liquid in the colon. In order to prevent injury to the patient, it is important that the amount of air delivered to the balloon 18 be carefully controlled. One way to acomplish this is to make the balloon out of a flexible non-stretchable material, thereby limiting its maximum size. This arrangement has the advantage of absolutely limiting the maximum size of the balloon, thereby positively preventing overinflation. However, such embodiment does not permit inflation of the balloon by varying amounts. Accordingly, to provide such absolute control of balloon 18 by different amounts, the conduit 21 leading to the balloon 18 is connected via a valve 22 to a piston and cylinder type syringe 23, to be described in greater detail below.

Referring to FIGS. 2 and 3, there is also shown a limiting means 19 in the form of a disc. This disc 19 may be necessary for at least two reasons. Firstly, in practice the end 17 of the tube and the balloon 18 may be subjected to varying asymmetrical forces tending to tilt the balloon, pulling it out of sealing contact with the walls of the rectum at the lower end thereof. Hence, to stabilize the balloon and maintain it in place to assure a good seal preventing fluids from passing between the exterior of the balloon and the walls of the rectum and anal canal, the disc 19 would be moved up against the exterior of the patient's anal opening and pressed thereagainst. Contrary to some previous limiting means used heretofore, I have found that stabilization of the balloon 18 is best achieved by the use of a generally circular, preferably oval, disc shape limiting means. A feature of the present invention is a construction whereby the disc 19 can be moved in one direction only and positively prevented against movement in the other direction, so that it can for example be slid to different positions, indicated as A, B and C at the graduations 20 in FIG. 2, to represent a heavy person, a normal person, and a thin person, respectively, the disc being so constructed that after moved to such positions, it cannot be moved back. While many different constructions can achieve this purpose, such as ridges with one sloped side and one narrow side, in the drawings I have shown attached to the disc 19 a sleeve 24 of for example a flexible plastic material extending for a distance relatively large as compared with the thickness of disc 19, such that movement of disc 19 to the right would be possible, but movement of the disc to the left would exert on the sleeve 24 frictional forces too great to be overcome with reasonable or usual forces.

To positively prevent expulsion of the tube and balloon 18, loops 30, 30a and 30b could be provided on the disc 19, each having attached thereto suitable straps 31, 31a and 31b, respectively, to be attached to a suitable waistband on the patient.

Referring to FIGS. 2 and 5, the balloon 18 is preferably of such a shape that when inflated it extends outwardly for a relatively large distance as compared for example to its dimension parallel to the axis of tube 16. There are two reasons for this. Firstly, such a shape minimizes the distance which the balloon, in its collapsed condition, must pass up into the anal canal before it is properly inserted. Secondly, such a balloon would provide a smaller volume, and hence a smaller surface area against which can act those muscles of the patient tending to expel the device. One disadvantage of such a balloon, however, is that in its natural, completely relaxed state it would tend to include residual air therein which should preferably be removed during insertion of the tube and balloon. However, complete exacuation of even this type of balloon is possible with the use of a piston and cylinder syringe control device and valve to be described below.

Figure 4:
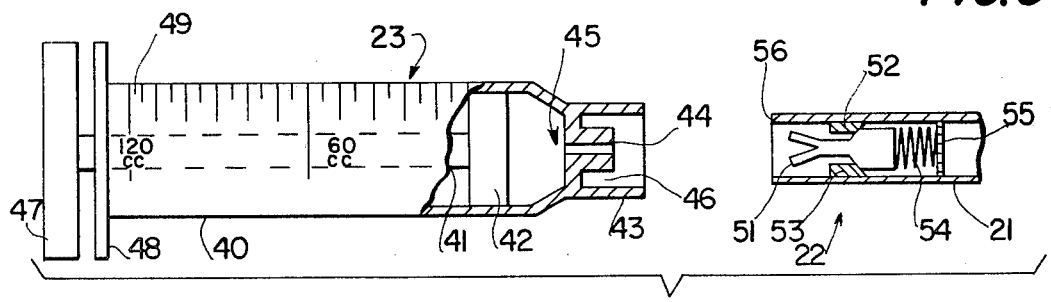
FIG. 4 is an enlarged view showing another portion of FIG. 1 with certain portions thereof shown in cross-section.

Referring to FIG. 4, the end of the conduit 21 includes a one-way valve 22 having a valve element 51 spring biased by a spring 54 into the closed condition wherein a surface 52 thereof firmly seats against a valve seat 53. The spring 54 rests at its other end against an open cage 55. A calibrated piston and cylinder syringe is provided for cooperating therewith. This device includes a cylinder 40 having a piston rod 41 extending therethrough with a piston 42 at the end thereof, which piston scalingly engages the inside wall of cylinder 40. On its side, the cylinder includes calibrated markings 49 for positively indicating the precise volume of air which has been introduced into and/or removed from the balloon 18 via conduit 21. Cylinder 40 includes a finger grip portion 48 and the piston rod 41 terminates at its outer end at a thumb push 47. In a manner which is known with respect to syringes, the operator would engage the portion 47 with the thumb and hold the finger grip portions 48 with the first two fingers of that hand. At its other end, the cylinder 40 includes a sealing flange 43 and the end would be closd by a structure including a raised central boss 44 with a fluid opening 45 passing therethrough. In practice, the end of the syringe would be engaged with the end of the conduit 21, whereby end 56 of the conduit would pass into the annular recess 46 between the boss 44 and the flange 43, thereby providing an air tight seal while the boss 44 engaged element 51, pushing it to the right, and unseating the valve. With this arrangement, the conduit 21 would then be closed at all times except when engaged by the syringe 23, at which time the valve would be opened for air flow in either direction.

The provision of a calibrated piston and cylinder syringe, and the use thereof for inflating a balloon in the present invention provides significant advantages. It permits the operator to accurately control the precise size of the balloon, which control is not otherwise possible since the balloon is not visible during the filling procedure. Heretofore, various devices such as limited capacity "puffers" have been used which provide a maximum quantity of air to the balloon to prevent overinflation. However, even these have not provided a way to precisely and visually measure the volume of air thus delivered to the balloon, and such previous means did not provide a way to precisely and exactly change the volume of the balloon after it has once been inflated with complete knowledge as to the amount of air added or removed. Hence, the operator is then able to precisely control the size of the balloon for different size patients and for different conditions within a given patient as well as positively protect against overinflation which could rupture the colon and kill the patient.

It is important that the valve mechanism positively be closed to prevent leakage from the balloon and to be positively opened for desired air flow through the conduit 21 in either direction. Only in this manner can the precise volume of air introduced be known as otherwise (for example if the valve were a one-way check valve opened by air pressure introduced into the balloon) the air would compress before opening the valve so that the operator would not have an accurate visual indication of the volume of air introduced.

Another feature of the present invention is the liquid solution to be used. Preferably the solution will be a known concentration soapy aqueous solution including approximately 20 cc of castile soap, or known additional volume of soap as required, in a volume of 1500 cc to 2000 cc of water with the addition thereto of a nonsoluble laxative in aqueous suspension. In practice, I have found it desirable to include such a laxative in a concentration suitable for a parficular patient's problems. In most cases I have found it suitable to add the laxative in an amount between 0.006 and 0.015 mg per cc of solution, although for different situations even this range could vary. I believe the provision of a castile soap solution with a laxative ingredient in suspension is new. Further, I believe the present invention includes a new vehicle for introducing such a laxative ingredient to the patient, namely by applying it in a procedure which completely fills and distends the colon, thereby carrying the laxative ingredient in a single step uniformly to the entire surface of the colon from the anal opening all the way to the cecum.

Figure 6:
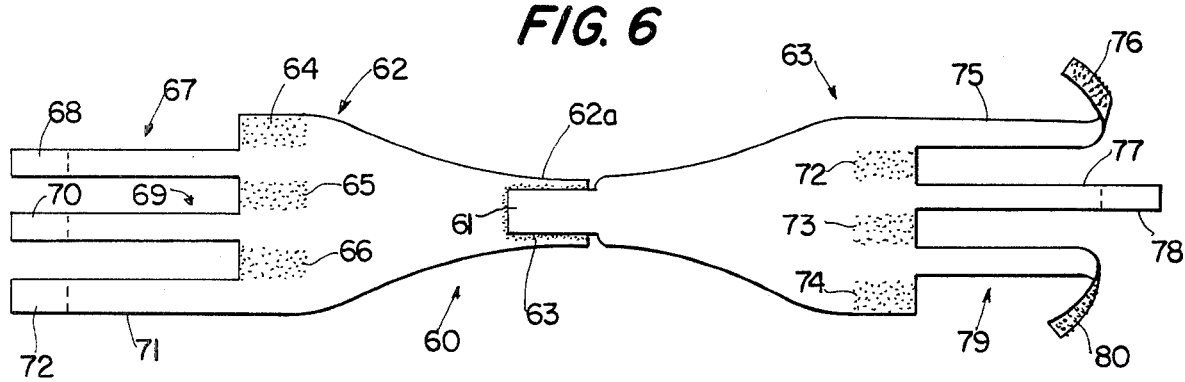
FIG. 6 illustrates a device laid out flat to be used for squeezing together the patient's buttocks.
Figure 8:
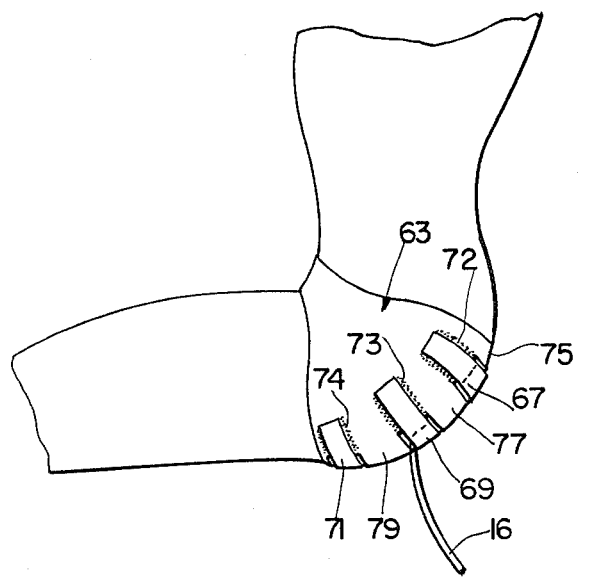
FIG. 8 illustrates the device of FIG. 6, on a patient, and viewed from the left side.
Figure 7:
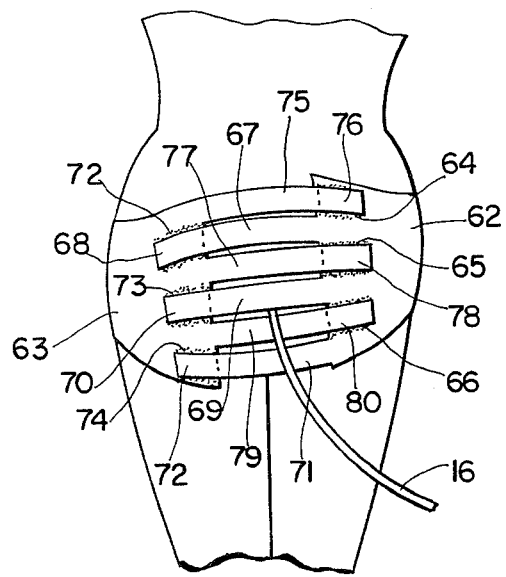
FIG. 7 illustrates the device of FIG. 6 on a patient, seen from the rear.

Another feature of the present invention is a means for squeezing the patient's buttocks together and against the perineum to prevent involuntary premature explusion of the balloon 18 and the liquid contained in the colon. Referring to FIGS. 6 through 8, and first to FIG. 6, there is shown a band 60 having a right side 62 and a left side 63. FIG. 6 views the outer side of the device, i.e., the side which would face away from the patient, when the device is in use. The left and right sides join along a front portion which is narrower than the remainder of the device so as not to inhibit the patient's bending his legs at the hips. When applied to the patient (in the manner as described below), the left and right sides must be rigidly attached together, as shown. However, for providing a quick release after the patient is finished with it, the left and right sides may be connected together at the front by a suitable quick release connection. In the preferred embodiment, this quick release means would comprise an overlapping Velcro connection, i.e., an extension 62a of the right side could comprise a felt pad which would be engaged by a Velcro hook pad on an extension 63a of left side 62. For a quick release, one would simply grab the end 61 of 63a and strip 63a from 62a. It will be apparent that other quick release means such as buckles, snaps or the like can be provided. The device includes a plurality of straps 67, 69 and 71 on the right side each having at its outer end a felt pad 68, 70 and 72, respectively (these pads are on the opposite side and hence not visible in FIG. 6). Between the planes of these straps there are provided Velcro hook pads 64, 65 and 66. On the left side there are provided further series of straps 75, 77 and 79, each with a similar felt pad 76, 78 and 80, respectively. While the pad 78 is not visible, the pads 76 and 80 are visible since the ends of straps 75 and 79 have been turned back. Also included are Velcro hook pads 72, 73 and 74 located between the planes of the straps 75, 77 and 79. It will be observed that the three straps on each side are spaced vertically from the planes of the three straps on the other side, and each of the six straps in fact lines up horizontally with a Velcro hook type pad on the opposite side.

In operation of the device 60, the tube 16 with balloon 18 would first be inserted. Referring to FIG. 7, the attendant would then apply device 60 by wrapping the device 60 around the patient, at first with none of the straps attached but with 62a and 63a secured together. To squeeze the buttocks together it is preferable to start from the bottom and work up. The operator would grap the two straps 71 and 79 and pull them tightly to the left and right, respectively, attaching the strap 71 by connecting the felt pad 72 to the Velcro hook pad 74. The operator would then grab the two straps 79 and 69 and pull them to the right and left, respectively, attaching the pad 80 to the Velcro hook pad 66. This process would be repeated until all of the straps were attached in this manner. While Velcro attachments are preferable, it will be apparent that other types of attaching means such as belt buckles and the like will also be operable in carrying out the present invention. With the tube 16, and balloon 18 and device 60 in place, the attendant would inflate the balloon and pull it down snugly against the lower end of the rectum adjacent the anal canal. The friction between the tube 16 and the straps which it engages (69 and 79 in FIGS. 7 and 8) will hold the balloon down into sealing engagement with the lower end of the rectum, thus performing the function ascribed above to disc 19, stabilizing the balloon in a fluid sealing position, in addition to its function of preventing involuntary expulsion of the balloon and tube.

Figure 9A:
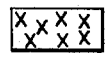
FIGS. 9A through 9E are schematic drawings of a human colon and illustrating the functioning thereof under different conditions.
Figure 9A:
Figure 9A:
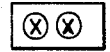
Figure 9A:
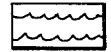
Figure 9A:
Figure 9A:
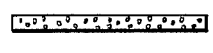
Figure 9A:
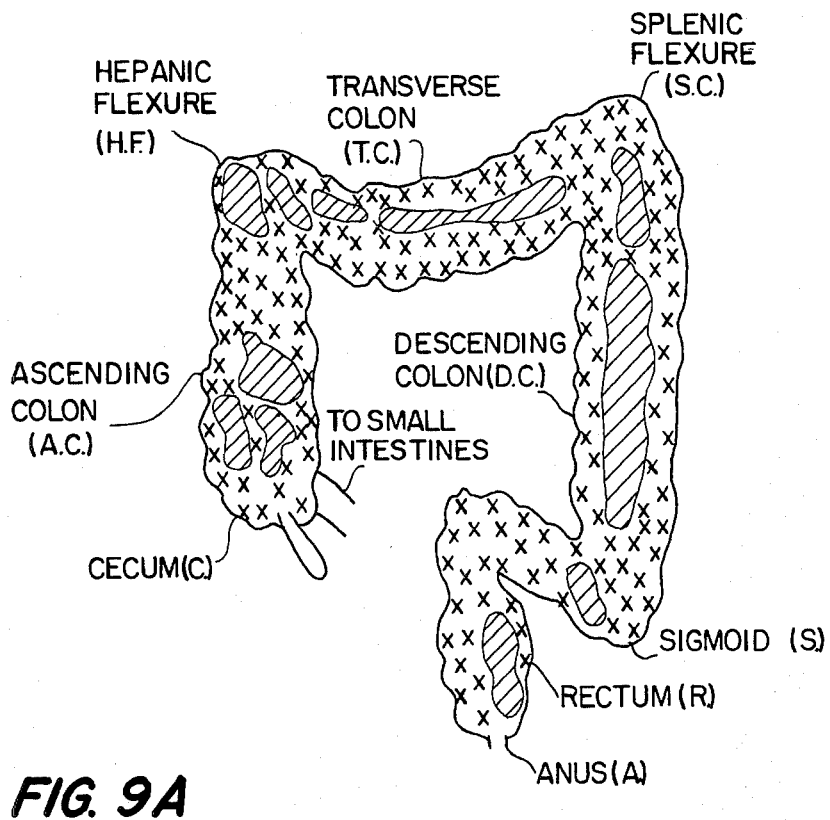

The method of the present invention and the operation of the above described system for carrying out the purposes of the invention is as follows. The method will be better understood with reference to FIGS. 9A through 9E. FIG. 9A illustrates the entire colon with the parts labeled, such labels followed with such representative letters which are those letters used in subsequent FIGS. 9B through 9E. FIG. 9A illustrates a colon filled with solid waste material, i.e., unloosened fecal matter and gas. The figure is intended to illustrate that the gas pockets can actually be located randomly at different locations although obviously as the patient moves to different positions, the gas will tend to rise to a high point.

Figure 9B:
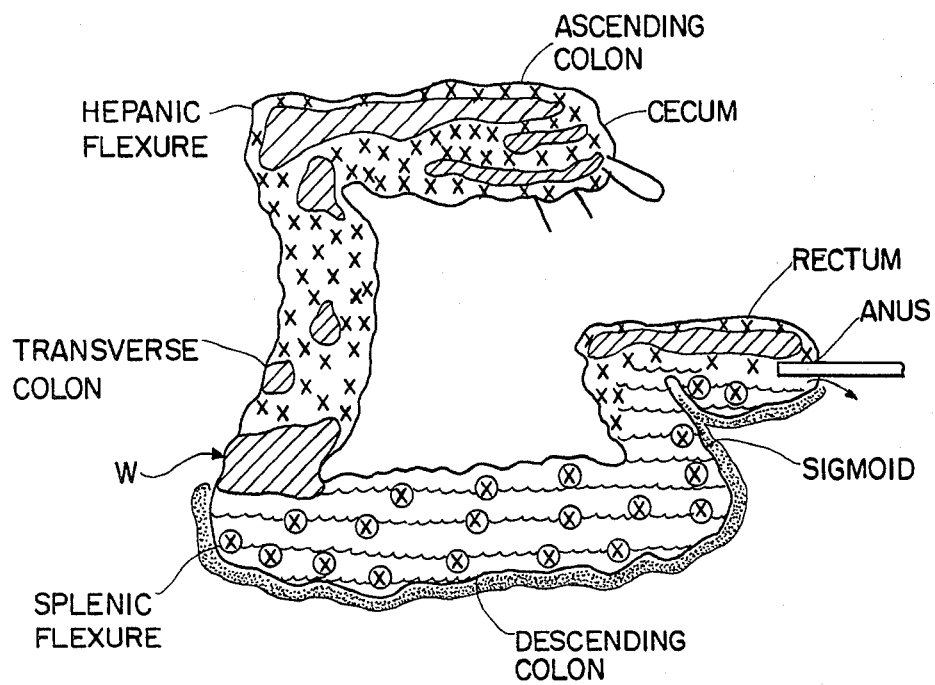

FIG. 9B illustrates the application of a conventional left side down enema to the colon filled as shown in FIG. 9A, and in particular it illustrates the colon after all of the liquid solution, usually between 500 cc and 1000 cc has been introduced into the patient's colon. In FIG. 9A the unloosened fecal matter was particularly difficult to move because it would tend to stick to the inside lining of the colon. In FIG. 9B the liquid moves along the side of the rectum, down the sigmoid and along the bottom of the descending colon (i.e., "bottom" as shown in FIG. 9B). The only portions of the colon lining which have been "washed", i.e. which have been subjected to the action of liquid in motion are the "lower" portions of the rectum and descending colon as shown in FIG. 9B with the wide gray border. The upper surfaces of the rectum and descending colon, as shown in FIG. 9B, may or may not have been washed, depending on the quantity of gas existing therein and possibly blocking contact of the liquid with those wall portions. However, the liquid cannot rise upwardly in the transverse colon. Firstly, it would have to oppose gravity just to travel in that direction. Secondly, gases which may have been located in the descending colon will now form a rather substantial gas lock. The body of solid fecal matter and the large gas lock tend to form a "wall" identified generally by the letter w in the figure. The liquid introduced in this manner may cause some distention in the wall of the rectum, sigmoid and descending colon, but not beyond those parts. In additional liquid is introduced, it will tend to leak outwardly around the tube and through the anal opening as shown by the arrow in the figure. Since under no circumstances can this liquid pass the area of the splenic flexure and rise in the transverse colon, the transverse and ascending colons will remain filled no matter how many enemas are given (and it is a common practice to give multiple enemas). Indeed, FIG. 9B illustrates the fallacy in believing that the colon is clean when, after a number of enemas, the solution runs out "clear". This would most likely indicate that only the rectum, sigmoid and descending colon have been cleansed, and that the liquid in the area of the splenic flexure, being blocked by the gas body in this area, simply did not touch the solid fecal matter in the transverse colon and ascending colon. Hence, the liquid would of course run out "clear".

When the left side down conventional procedure has been completed, the entire mass in the ascending and transverse colon must then be cleaned by oral laxatives with all of their attendant disadvantages as discussed above or remain in the colon to harden or "impact" or soil the bed if the patient is fecally incontinent.

Figure 9C:
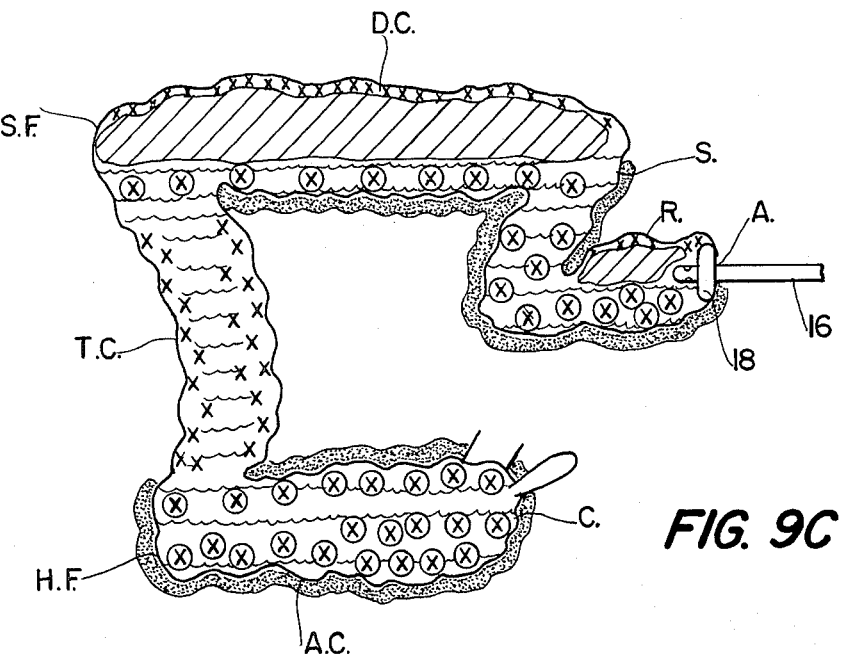
Figure 9D:
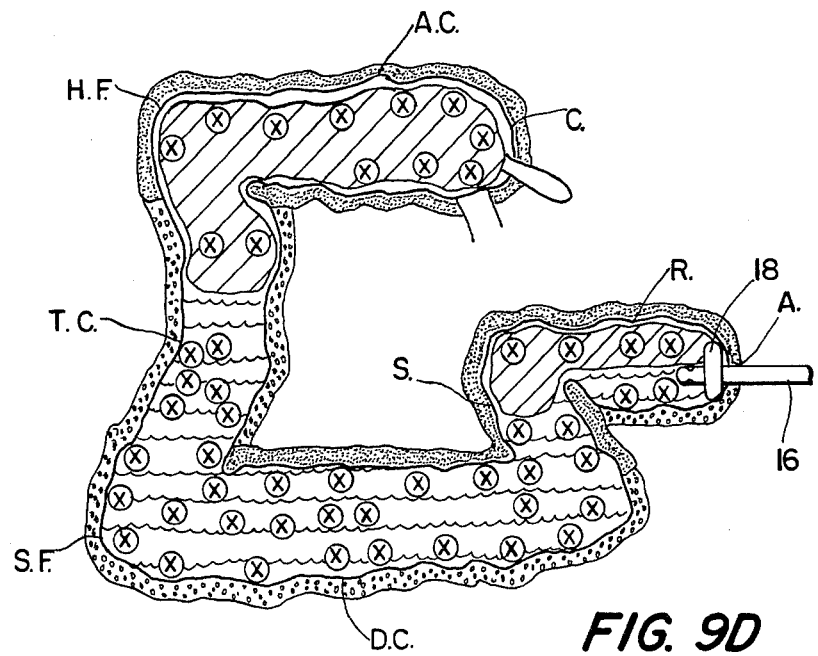
Figure 9E:
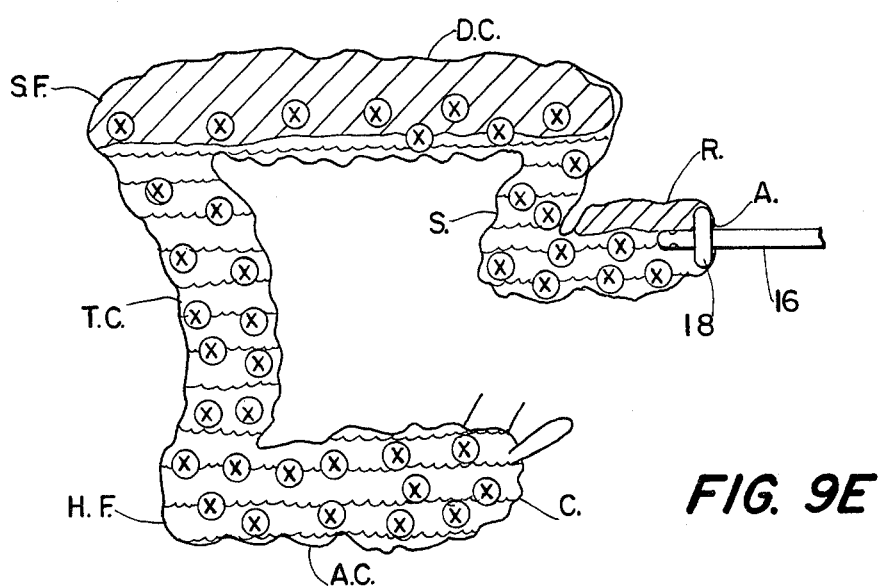

FIGS. 9C through 9E illustrate the functioning of the colon in the operation of the present invention.

Figure 5A:
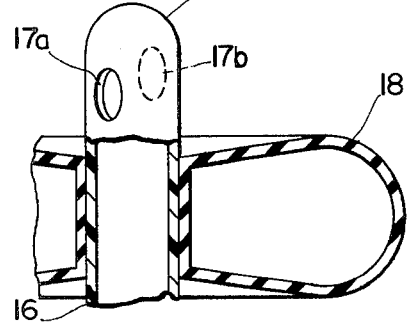
FIGS. 5A, 5B and 5C are enlarged views of the balloon of FIGS. 1-3, but showing different inflated positions thereof.
Figure 5B:
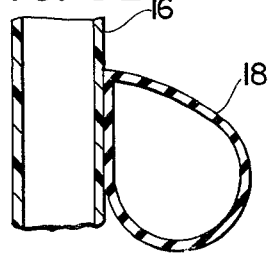
Figure 5C:
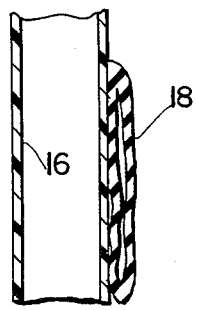

With clamp 25 closing tube 16, an appropriate volume of liquid solution would be introduced through opening 13 into bag 11. The balloon 18 would then be completely evacuated. Referring to FIGS. 5A through 5C. FIG. 5A illustrates the balloon in its completely inflated condition and FIG. 5B illustrates the balloon in its completely relaxed condition. However, the residual air still located therein should preferably be removed prior to insertion of the tube. For this purpose the conduit 21 can be connected to the syringe 23 and the piston 42 withdrawn thereby evacuating the balloon 18 as shown in FIG. 5C. The syringe would then be disconnected from the valve 22, permitting the valve to close, and the piston 42 would then be pulled back enough to provide precisely the desired amount of air to inflate balloon 18 which might be for example 60 or 120 cc. With the attendant preferably standing in front of the patient, the tube is then inserted into the patient. If the device 60 is to be used, it is applied at this time in the manner described above. With the syringe 23 attached again to the conduit 21 the piston 42 is moved forwardly, introducing precisely the correct quantity of air, e.g. 60 cc to 120 cc, the exact amount being visually observed by noting the calibrated markings 49 on syring 40. If device 60 has not yet been applied, the disc 19 may now be slid along tube 17 to the correct position to stabilize and secure the seal of balloon 18. To prevent expulsion of balloon 18, the straps 31, 31a and 31b could now be connected to a waistband or the like on the patient. Alternatively to said straps, the device 60 could now be applied, this time serving only the function of preventing involuntary expulsion of the balloon.

With the patient on his right side, the clamp 25 is then opened, permitting the liquid solution to flow through the tube 16. Referring to FIG. 9C, this quantity of liquid, prevented from escaping by balloon 18, flows along the rectum, up the sigmoid and along the "bottom" of the descending colon (gas having risen to the top thereof) and then down the transverse colon, displacing upwardly any gases located therein, around the hepatic flexure, and along the ascending colon to the cecum. As the liquid solution is initially being introduced, some distention may occur in the vicinity of the rectum, the sigmoid, descending, transverse and ascending colon. However, operable levels of distention throughout the colon do not occur until after a sufficient quantity of liquid has been introduced to the colon to fill the colon throughout its length, but for the space taken up by the solid fecal matter and gases already located therein. As shown in FIG. 9C, at this time those walls bounded by the wide gray margin, namely the lowermost part of the rectum, the sigmoid, the "bottom" of the descending colon and the ascending colon have most likely been contacted by a sufficient amount of liquid solution in motion to have been agitated or "washed". As distention of the walls occurs along with this washing action, the lubricating action of the castile soap in the liquid will cause the stool and mucus attached to the walls of the colon to soften, to fragment and to detach from the lining of the colon, and to become lubricated. Further, as the fecal matter or "stool" is detached, the laxative within the liquid solution is permitted to contact the lining of the colon, causing it to contract. At this time it cannot be certain whether the entire lining of the colon has been contacted by the liquid solution. For example as shown in FIG. 9C, gases collected at the top of the rectum and descending colon may have prevented the liquid solution from removing fecal matter and mucus from the lining of these places. Similarly, as the liquid ran down the transverse colon, it cannot be certain whether the walls of the transverse colon were "washed" sufficiently to remove stool and mucus therefrom. To assure that the liquid "washes" and that the laxative contacts the entire surface area of the colon lining, the patient may then be rolled over to his left side, creating the situation shown in FIG. 9D. Now the liquid flows to the "down" side of all segments of the colon assuring contact with and washing of all areas of the lining bordered by the speckled margin in FIG. 9D. The swashing action of the liquuid back and forth through the transverse colon as the patient is moved from his right side to his left side (and this action of right side to left side may be repeated as many times as necessary) will surely have caused the necessary washing of the entire surface area of the lining of the colon with the resultant softening, fragmenting and lubricating of the attached fecal matter and the consequent contacting of the entire lining with the laxative containing liquid.

Finally, the patient will be rolled back to the right side, as shown in FIG. 9E, all lining surfaces having been contacted by the liquid so that all of the fecal matter and mucus material within the colon will have been loosened, softened, fragmented and lubricated, and the entire lining of the colon, having been contacted with the laxative, will be capable of undergoing contraction to expel all solid liquid and gaseous materials contained therein.

The volume of liquid solution will vary depending on several factors, including the size of the patient, the amount of solid and gaseous materials already present in the colon prior to introduction of the liquid solution, and the condition of the patient's colon. For example, while I have indicated previously that the 1500 cc to 3000 cc of liquid solution would normally be used, even less than 1500 cc may be necessary to fill the colon in the case of a child, infant, or person who has had a portion of his colon removed.

The advantage of bringing the laxative to the entire lining throughout the entire colon is accomplished expecially well in the course of the present invention. The laxative, to carry out is stimulating function, must contact the lining itself, and not merely the mucus layer on the lining. The colon cleansing technique of the present invention, with its ability to clean off the entire colon lining, assures that the mucus layer is detached along with the stool to thereby fully expose the lining itself to the laxative.

It was suggested above that the patient be rolled to the left side to provide further agitation to enhance "washing" of the walls of the colon and thereby better effect detachment of the stool and mucus from the lining. However, such agitation can be carried out in other ways. For example direct in and out motion of the anterior abdominal wall can be provided by direct hand pressure or by a vibrator placed against the abdominal wall. Also liquid can be moved in and out of the colon by having the fluid located in the colon connected through the tube to a fluid column which can then be raised or lowered, resulting in the fluid being introduced into and temporarily removed from the colon. Alternatively, the balloon 18 can be slightly inflated and deflated at proper frequency to cause a wave or churning action of the liquid in the colon. Or alternatively ultra sound procedures can be utilized to effect agitation by vibration, for example by having the liquid run through the tube and to a fluid column which can be acted upon.

Whatever mechanical agitation is used, when it is completed, the patient is taken to a proper receptacle, the device 60, if used, is released by uncoupling extension 63a from 62a, the balloon 18 is fully deflated and removed with the tube 16, and at this time the patient can expel the entire contents of the colon.

Although the invention has been described in considerable detail with respect to a preferred embodiment thereof and a preferred operation thereof, it will be apparent that the invention is capable of numerous modifications and variations which will be apparent to those skilled in the art.

I claim:

1. A method of cleansing a person's entire colon of solid and/or liquid materials therein, comprising the following steps:

in the absence of any prior colon cleansing treatment by means of orally taken laxatives, filling the colon completely with an aqueous liquid by introducing the liquid through the anal opening in sufficient quantity to fill the colon to the extent of distending the wall of the colon from the rectum to the cecum, wherein the liquid includes an ingredient which assists the liquid in loosening and removing the solid material, assuring that the aqueous liquid is retained in the person's colon for a predetermined period of time, while said liquid is being retained in the colon, causing motion of the liquid back and forth through the person's colon, such that the liquid moves relative to the walls of the colon to facilitate removal fo solid materials from the colon lining, and removing all obstructions to permit the person to expel substantially the entire quantity of solids and liquids from the colon.

2. A method according to claim 1, wherein said ingredient includes a wetting agent in said aqueous liquid, and the step of causing said motion aids in bringing the wetting agent into complete contact with the entire lining of the large intestine.

3. A method according to claim 2, said wetting agent being castile soap.

4. A method according to claim 1, wherein said ingredient includes a laxative in said aqueous liquid, and the step of causing said motion aids in bringing the laxative into complete contact with the entire lining of the large intestine.

5. A method according to claim 1, wherein the ingredient includes including both a wetting agent and a laxative in said aqueous liquid, and the step of causing said motion aids in bringing the wetting agent and the laxative into contact with the entire lining of the large intestine.

6. A method according to claim 5, wherein the step of causing motion of the liquid within the person's large intestine comprises rolling the person over to his or her left side, and then back to his or her right side to assist in bringing the wetting agent and laxative into contact with the entire lining of the large intestine.

7. A method according to claim 6, wherein the wetting agent is castile soap and the laxative is Bisacodyl.

8. A method according to claim 6, wherein the liquid is introduced into the person theough a tube, and the step of closing off the anus comprises inflating a balloon mounted on the tube and located just inside the anus.

9. A method according to claim 8, including inflating the balloon by an exactly ascertainable amount by introducing fluid into the balloon using a device which is calibrated to visibly indicate the volume of fluid delivered thereto, and maintaining the selected volume in the balloon unless more is added or removed by said calibrated device.

10. A method according to claim 9, wherein the calibrated device is a piston and cylinder syringe, and the calibrations show the exact change in volume in the syringe, and hence also in the balloon, upon relative movement of the piston and cylinder.

11. A method according to claim 1, wherein the step of causing motion of the liquid within the person's large intestine comprises rolling the person over to his or her left side, and then back to his or her right side.

12. A method of cleansing a person's entire colon of solid and/or liquid materials therein, comprising the following steps:
in the absence of any prior colon cleansing treatment by means of orally taken laxatives, filling the colon completely with an aqueous liquid by introducing the liquid through the anal opening in sufficient quantity to fill the colon to the extent of distending the wall of the colon from the rectum to the cecum, wherein the liquid includes an ingredient which assists the liquid in loosening and removing the solid material,
placing the person in a right side down position during introduction of at least the last 1000 ml of aqueous liquid,
assuring that the said aqueous solution is retained in the person's colon for a predetermined period of time as the liquid loosens the fecal material in the colon,
while said liquid is being retained in the colon, causing motion of the liquid back and forth through the person's colon, such that the liquid moves relative to the walls of the colon to facilitate removal of solid materials from the colon lining,
and removing all obstructions to permit the person to expel substantially the entire quantity of solids and liquids from the colon.

13. A method according to claim 12, in which the ingredient includes a wetting agent such as castile soap.

14. A method according to claim 12, wherein said ingredient further includes a wetting agent and a laxative in the aqueous liquid and said filling step includes reaching and contacting substantially the entire lining of the large intestine with said laxative.

15. A method according to claim 14, said motion causing step including rolling the person to the left side down position and back to the right side down position.

16. A method according to claim 14, wherein the laxative is Bisacodyl.

17. A method according to claim 16, wherein the concentration of the Bisacodyl within the aqueous solution is 0.005 to 0.015 mg per cc of solution.

18. A method according to claim 14, wherein the filling step comprises introducing the liquid through a tube which enters the anus and has an inflatable balloon near the end thereof, and inflating the balloon which performs the step of closing off the anus to prevent escape of liquid.

19. A method according to claim 18, including inflating the balloon by an exactly ascertainable amount by introducing fluid into the balloon using a device which is calibrated to visibly indicate the volume of fluid delivered thereto, and maintaining the selected volume in the balloon unless more is added or removed by said calibrated device.

20. A method according to claim 19, wherein the calibrated device is a piston and cylinder syringe, and the calibrations show the exact change in volume in the syringe, and hence also in the balloon, upon relative movement of the piston and cylinder.

21. In the process of cleansing a person's colon, a method for administering a laxative comprising:
filling the person's colon completely with an aqueous liquid by introducing the liquid through the anal opening in sufficient quantity to fill the colon from the cecum to the rectum,
including in the liquid a laxative ingredient distributed uniformly throughout the liquid in effective concentrations,
said step of administering the laxative including adding a laxative ingredient to a body of liquid, and then introducing the laxative containing liquid into the person's large intestine until the liquid entirely fills the large intestine from the rectum to the cecum, sufficiently to commence distension,
assuring that the liquid containing the laxative ingredient is retained in the person's colon for a predetermined period of time, during which the laxative contacts the lining of the colon throughout its entire length, to thereby cause the uniform application of laxative, throughout the entire length of the colon, and
removing all obstructions to permit the person to expel solid and liquid materials from the colon.

22. A method according to claim 21, said laxative being Bisacodyl in a concentration of 0.005–0.015 mg. per cc of aqueous solution.

23. A process according to claim 21, including causing motion of the liquid which fills the large intestine to further aid in bringing the laxative uniformly into contact with the entire large intestine lining.

24. A method according to claim 21, wherein the laxative is Bisacodyl.

25. A method of cleansing a person's entire colon of solid and/or liquid materials therein comprising the following steps:

in the absence of any prior colon cleaning treatment by means of orally taken laxatives, filling the person's colon completely with an aqueous liquid by introducing the liquid through the anal opening in sufficient quantity to fill the colon to the extent of distending the wall of the colon from the rectum to the cecum, including in the liquid a miscible wetting agent, such that the wetting agent comes into contact with the lining of the colon throughout its entire length, assuring that the aqueous liquid is retained in the person's colon for a predetermined period of time during which the wetting agent detaches, fragments and lubricates solid fecal material throughout the entire length of the colon, while said liquid is being retained in the colon, causing motion of the liquid back and forth through the person's colon, such that the liquid moves relative to the walls of the colon to facilitate removal of solid materials from the colon lining, and removing all obstructions to permit the person to expel substantially the entire quantity of solids and liquids from the colon.

26. A method according to claim 25, said wetting agent being castile soap.

27. A method according to claim 25, wherein said filling step includes including a laxative in said aqueous solution.

28. A method according to claim 25, wherein the step of causing motion of the liquid within the colon comprises rolling the person over to his or her left side and then back to his or her right side.

29. A method according to claim 25, wherein the step of retaining the liquid in the colon includes inserting the liquid through a tube having an inflatable balloon on the outside thereof, and inflating the balloon, prior to introducing the liquid, with the balloon located in the rectum adjacent to the anus.

30. A method of cleansing a person's entire colon of solid and/or liquid materials therein, comprising the following steps:

in the absence of any prior colon cleansing treatment by means of orally taken laxatives, filling the person's entire colon completely with an aqueous liquid by introducing the liquid through the anal opening in sufficient quantity to fill the colon to the extent of distending the wall of the colon from the rectum to the cecum, wherein the liquid includes an ingredient which assists the liquid in loosening and removing the solid material, placing the person in a right side down position during introduction of at least the last 1000 ml of the aqueous liquid, retaining the liquid in the colon by inserting the liquid through a tube having an inflatable balloon on the outside thereof, and inflating the balloon, prior to introducing the liquid, with the balloon located in the rectum adjacent the anus, while said liquid is being retained in the colon, causing motion of the liquid back and forth through the person's colon, such that the liquid moves relative to the walls of the colon to facilitate removal of solid materials from the colon lining, and deflating the balloon and removing the balloon and tube to permit the person to expel solid and liquid materials from the colon.

31. A method according to claim 30, including filling the balloon with an exactly determinable volume of fluid by moving fluid into the balloon using a calibrated device with calibrations thereon to show quantitatively the exact volume of fluid moved into the balloon.

32. A method according to claim 31, including maintaining complete control at all times of the amount of fluid in the balloon by using, in the line between the calibrated device and the balloon, a valve always biased towards the closed position by a spring and by fluid pressure within the balloon and openable to either add or remove fluid to or from the balloon only by moving an element of the valve by engaging it with said calibrated device in a position to either introduce fluid into or remove fluid from the balloon.

33. A method according to claim 30, wherein the calibrated device is a piston and cylinder syringe, and the calibrations show the exact change in volume in the syringe, and hence also in the balloon, upon relative movement of the piston and cylinder.

34. A method according to claim 33, wherein the valve is located in the line at the end thereof remote from the balloon, and the piston and cylinder syringe includes a projection thereon which opens the valve when inserted into said remote end of the line.

35. A method according to claim 30, wherein the balloon is of a material having sufficient rigidity such that in its fully relaxed condition it contains residual air therein, and prior to inserting the balloon, including the step of opening the valve and fully collapsing the balloon by moving the piston relative to the cylinder in a direction opposite from that direction applicable in inflating the balloon.

36. A method of cleansing a person's entire colon of solid and/or liquid materials therein comprising the following steps:

in the absence of any prior colon cleansing treatment by means of orally taken laxatives filling the colon completely with an aqueous liquid by introducing the liquid through the anal opening in sufficient quantity to fill the colon to the extent of distending the wall of the colon from the rectum to the cecum, including at least one of (1) a miscible wetting agent and/or (2) a laxative ingredient uniformly distributed in the liquid which is introduced into the person's colon assuring that the liquid with the wetting agent and/or laxative is retained in the person's colon for a predetermined period of time, and while the liquid is thus retained, causing motion of the liquid back and forth through the colon, such that the liquid moves relative to the colon wall to facilitate contact of the ingredient and the liquid within the colon wall to enhance removal of the solid materials from the colon lining, and removing obstructions to permit the person to expel substantially the entire quantity of solids and liquids from the colon.

37. A method according to claim 36, wherein the aqueous liquid includes both a miscible wetting agent and a laxative, and wherein the miscible wetting agent is castile soap.

38. A method according to claim 37, wherein said laxative is Bisacodyl.

39. A method according to claim 37, wherein the step of retaining the liquid in the colon includes inserting the liquid through a tube having an inflatable balloon on the outside thereof, and inflating the balloon, prior to introducing the liquid, with the balloon located in the rectum adjacent to the anus.

40. A method according to claim 39, including filling the balloon with an exactly determinable volume of fluid by moving fluid into the balloon using a calibrated device with calibrations thereon to show quantitatively the exact volume of fluid moved into the balloon.

41. A method according to claim 40, including maintaining complete control at all times of the amount of fluid in the balloon by using, in the line between the calibrated device and the balloon, a valve always biased towards the closed position by a spring and by fluid pressure within the balloon and openable to either add or remove fluid to or from the balloon only by moving an element of the valve by engaging it with said calibrated device in a position to either introduce fluid into or remove fluid from the balloon.

42. A method of cleansing a person's entire colon of solid and/or liquid materials therein, comprising the following steps:
in the absence of any prior colon cleansing treatment by means of orally taken laxatives, and with the person in a right side down position, filling the person's colon with an aqueous liquid by introducing the liquid through the anal opening in sufficient quantity to fill the colon to the extent of distending the wall of the colon from the rectum to the cecum,
including in the liquid which is introduced into the colon a miscible wetting agent and a laxative in suspension in the liquid,
said introducing being performed by delivering the liquid through a tube having an inflatable balloon on the outside thereof,
retaining the liquid in the person's colon by inflating the balloon, prior to introduction of the liquid, with the balloon located in the rectum adjacent the anus,
while the liquid is being retained within the person's colon, causing a motion of the liquid back and forth through the person's colon to bring the wetting agent and laxative into contact with the entire lining of the colon to facilitate removal from the colon lining, fragmentation, and lubrication of the solid materials, and to facilitate expulsion of the solid and liquid materials by the action of the entire colon wall, and
deflating the balloon and removing the tube and balloon from the person's anal opening to permit the person to expel substantially the entire solid and liquid content of the colon.

43. A method according to claim 42, wherein the laxative is Bisacodyl.

44. A method according to claim 43, wherein the wetting agent is castile soap.

45. A method according to claim 44, including filling the balloon with an exactly determinable volume of fluid by moving fluid into the balloon using a calibrated device with calibrations thereon to show quantitatively the exact volume of fluid moved into the balloon.

46. A method according to claim 45, including maintaining complete control at all times of the amount of fluid in the balloon by using, in the line between the calibrated device and the balloon, a valve always biased towards the closed position by a spring and by fluid pressure within the balloon and openable to either add or remove fluid to or from the balloon only by moving an element of the valve by engaging it with said calibrated device in a position to either introduce fluid into or remove fluid from the balloon.

47. In a method for cleaning a person's entire colon of solid and liquid materials therein, wherein a sufficient quantity of aqueous liquid is introduced into the person's colon to entirely fill it, and a balloon is used to hold the liquid therein, a procedure for controlling the size of the balloon just inside of the anal opening which prevents the escape of the liquid therein, comprising:
introducing into the person's anus just prior to introduction of the liquid a tube with an expandable balloon near the end thereof,
filling the balloon with an exactly determinable volume of fluid by moving fluid into the balloon using a calibrated device with calibrations thereon to show quantitively the exact volume of fluid moved into the balloon,
maintaining complete control at all times of the amount of fluid in the balloon by using, in the line between the calibrated device and the balloon, a valve always biased towards the closed position by a spring and by fluid pressure within the balloon and openable to either add or remove fluid to or from the balloon only by moving an element of the valve by engaging it with said calibrated device in a position to either introduce fluid into or remove fluid from the balloon
and wherein the balloon is of a material having sufficient rigidity such that in its fully relaxed condition it contains residual air therein, and prior to inserting the balloon, including the step of opening the valve and fully collapsing the balloon by moving the piston relative to the cylinder in a direction opposite from the direction applicable in inflating the balloon.

48. A method according to claim 47, wherein the calibrated device is a piston and cylinder syringe, and the calibrations show the exact change in volume in the syringe, and hence also in the balloon, upon relative movement of the piston and cylinder.

49. A method according to claim 48, wherein the valve is located in the line at the end thereof remote from the balloon, and the piston and cylinder syringe includes a projection thereon which opens the valve when inserted into said remote end of the line.

50. A method of cleansing a person's entire large intestine comprising the following steps:
in the absence of any prior colon cleaning treatment by means of orally taken laxatives, inserting into the person's anal opening a tube having an inside diameter of appropriate size for the flow therethrough of an aqueous liquid and having thereon near the end thereof an inflatable balloon in a collapsed condition,
inflating the balloon sufficiently to seal the person's anus around the tube by injecting fluid into the balloon by the use of an inflatable device located outside of the person and leading via a conduit to the balloon,
with the person laying on his or her right side, introducing the liquid containing a wetting agent into the large intestine through the tube,
continuing to introduce said liquid until there has been introduced into the person a volume of liquid sufficient to fill the entire large intestine from the cecum to the rectum, and to distend the large intestine throughout its length to loosen the fecal matter throughout the entire length of the large intestine, holding the full introduced volume of said liquid in the person for a limited period of time to permit interaction of the liquid with the fecal matter and the wall of the large intestine over the entire length thereof, while said liquid is being retained in the colon, causing motion of the liquid back and forth through the person's colon, such that the liquid moves relative to the walls of the colon to facilitate removal of solid materials from the colon lining, and deflating the balloon and removing the tube and balloon to permit the person to expel the liquid and fecal matter.

51. A method according to claim 50, wherein the introducing step includes introducing said liquid with a laxative being non-soluble and held in suspension thereon.

52. A method according to claim 51, wherein the laxative is Bisacodyl.

53. A method according to claim 52, wherein the concentration of Bisacodyl in the solution is between 0.005 and 0.015 mg per cc.

54. A method according to claim 50, wherein the inserting step includes inserting a tube having an outside diameter of approximately ¼ inch and an inside diameter of about 3/16 inch.

55. A method according to claim 50, and the ballon being located close to that end of the tube inserted into the patient.

56. A method according to claim 50, and the tube being of a soft flexible material.

57. A method according to claim 50, said inflating step including inflating the balloon to a generally disc shape wherein the distance that the balloon extends out from the outer wall of the tube exceeds the dimension of the balloon parallel to the axis of the tube.

58. A method according to claim 50, wherein the introducing step includes holding the liquid in a bag having a capacity of at least 1500 cc and communicating at its lower end with the tube.

59. A method according to claim 58, said bag having a capacity of at least 2500 cc.

60. A method according to claim 58, wherein the length of the tube from the bag to its end within the patient is limited to 60 to 75 cm.

61. A method according to claim 50, wherein the inflating step includes observing and measuring the amount of air delivered from the inflating device into the balloon, and using a valve in the conduit between the inflating device and the balloon, which valve is positively opened during inflation and positively closed thereafter.

62. A method according to claim 50, wherein the method further includes the step of having the attendant performing said steps positioned in front of the patient.

* * * * *